(12) United States Patent
Peters

(10) Patent No.: US 11,234,630 B2
(45) Date of Patent: Feb. 1, 2022

(54) CARDIAC HEALTH ASSESSMENT SYSTEMS AND METHODS

(71) Applicant: Cortery AB, Domsten (SE)

(72) Inventor: Filip Ludwig Peters, Domsten (SE)

(73) Assignee: Acorai AB, Domsten (SE)

( * ) Notice: Subject to any disclaimer, the term of this patent is extended or adjusted under 35 U.S.C. 154(b) by 60 days.

(21) Appl. No.: 16/946,025

(22) Filed: Jun. 3, 2020

(65) Prior Publication Data
US 2021/0378537 A1    Dec. 9, 2021

(51) Int. Cl.
| | | |
|---|---|---|
| *A61B 5/00* | (2006.01) | |
| *A61B 5/361* | (2021.01) | |
| *G16H 10/60* | (2018.01) | |
| *G16H 40/67* | (2018.01) | |
| *G16H 50/20* | (2018.01) | |
| *A61B 5/11* | (2006.01) | |
| *A61B 5/332* | (2021.01) | |

(52) U.S. Cl.
CPC ............ *A61B 5/361* (2021.01); *A61B 5/0006* (2013.01); *A61B 5/1102* (2013.01); *A61B 5/332* (2021.01); *A61B 5/6823* (2013.01); *G16H 10/60* (2018.01); *G16H 40/67* (2018.01); *G16H 50/20* (2018.01); *A61B 2560/0431* (2013.01)

(58) Field of Classification Search
CPC .................. A61B 5/0404; A61B 5/046; A61B 2560/0431
See application file for complete search history.

(56) References Cited

U.S. PATENT DOCUMENTS

| | | | |
|---|---|---|---|
| 2010/0042008 A1* | 2/2010 | Amitai ................. | A61B 5/6826 600/509 |
| 2015/0065814 A1* | 3/2015 | Kapoor ................ | A61B 5/0022 600/301 |
| 2015/0216448 A1* | 8/2015 | Lotan ...................... | A61B 7/00 600/538 |
| 2018/0146911 A1* | 5/2018 | Teicher ................ | G06T 7/0012 |
| 2019/0104238 A1* | 4/2019 | Barros ....................... | A45F 5/00 |
| 2019/0117068 A1* | 4/2019 | Thomson .............. | A61B 5/0006 |
| 2020/0029834 A1* | 1/2020 | Tang ..................... | A61B 5/0535 |

\* cited by examiner

*Primary Examiner* — Rex R Holmes
*Assistant Examiner* — Sana Sahand
(74) *Attorney, Agent, or Firm* — Silver Legal LLC; Jarrett L. Silver

(57) ABSTRACT

A cardiac health assessment system and method for use with a handheld electronic device. The cardiac health assessment system includes an electronic device case (EDC), a plurality of electrodes, and a circuit board. The EDC secures the handheld electronic device. The electrodes include a first ECG electrode, a second ECG electrode, and a third electrode. The first ECG electrode is placed on an outer surface of the EDC. The second ECG electrode and the third electrode are placed on each side of the EDC to facilitate a thumb and fingers of a user to be placed on the handheld electronic device. The electrodes capture data indicative of the cardiac health of the user. The circuit board includes a microphonic sensor, an Inertial Measurement Unit (IMU) sensor, and a microcontroller. The microphonic sensor and IMU sensor capture cardiac health data. The microcontroller transmits cardiac health data to the handheld electronic device.

11 Claims, 11 Drawing Sheets

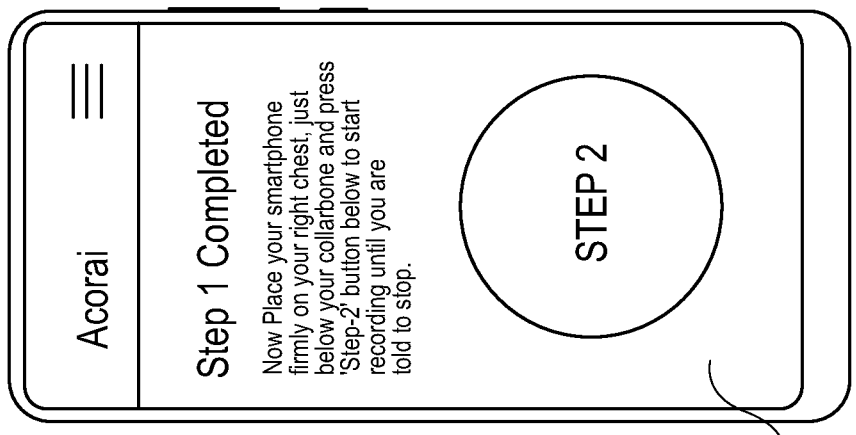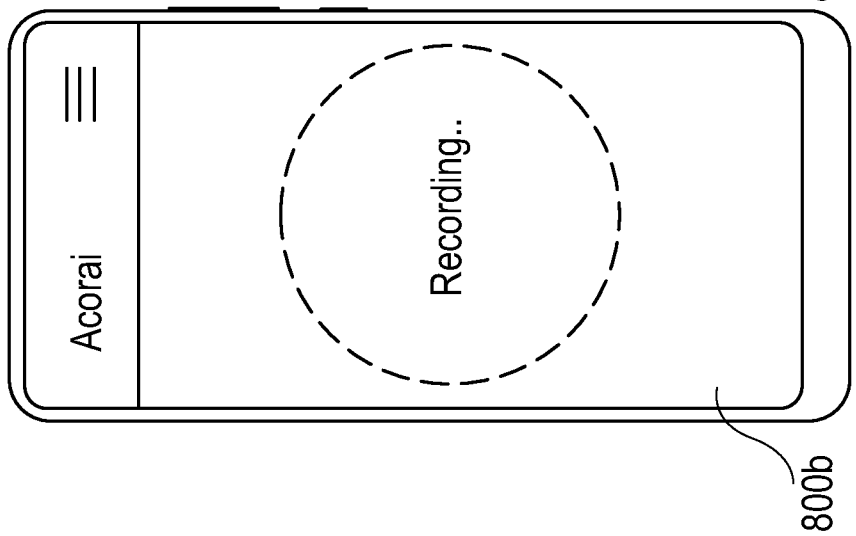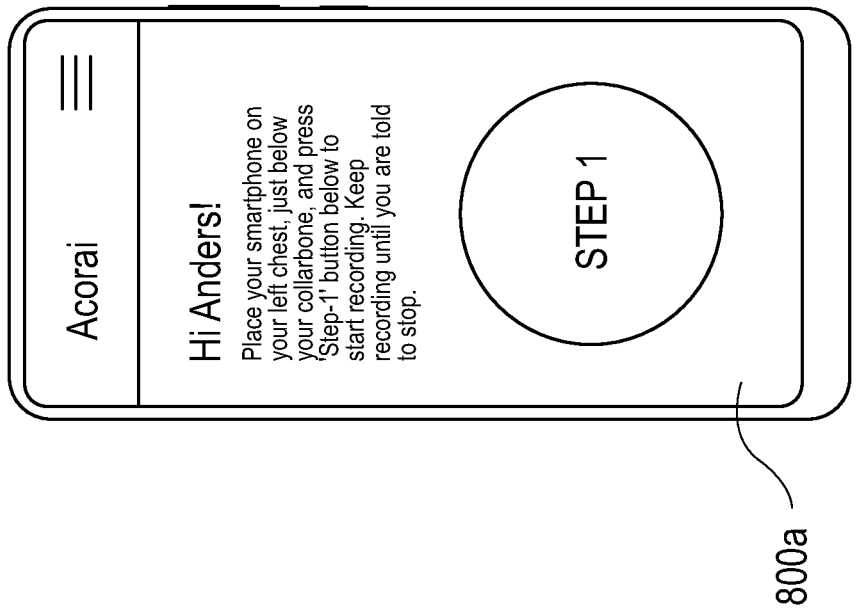
FIG. 8C
FIG. 8B
FIG. 8A

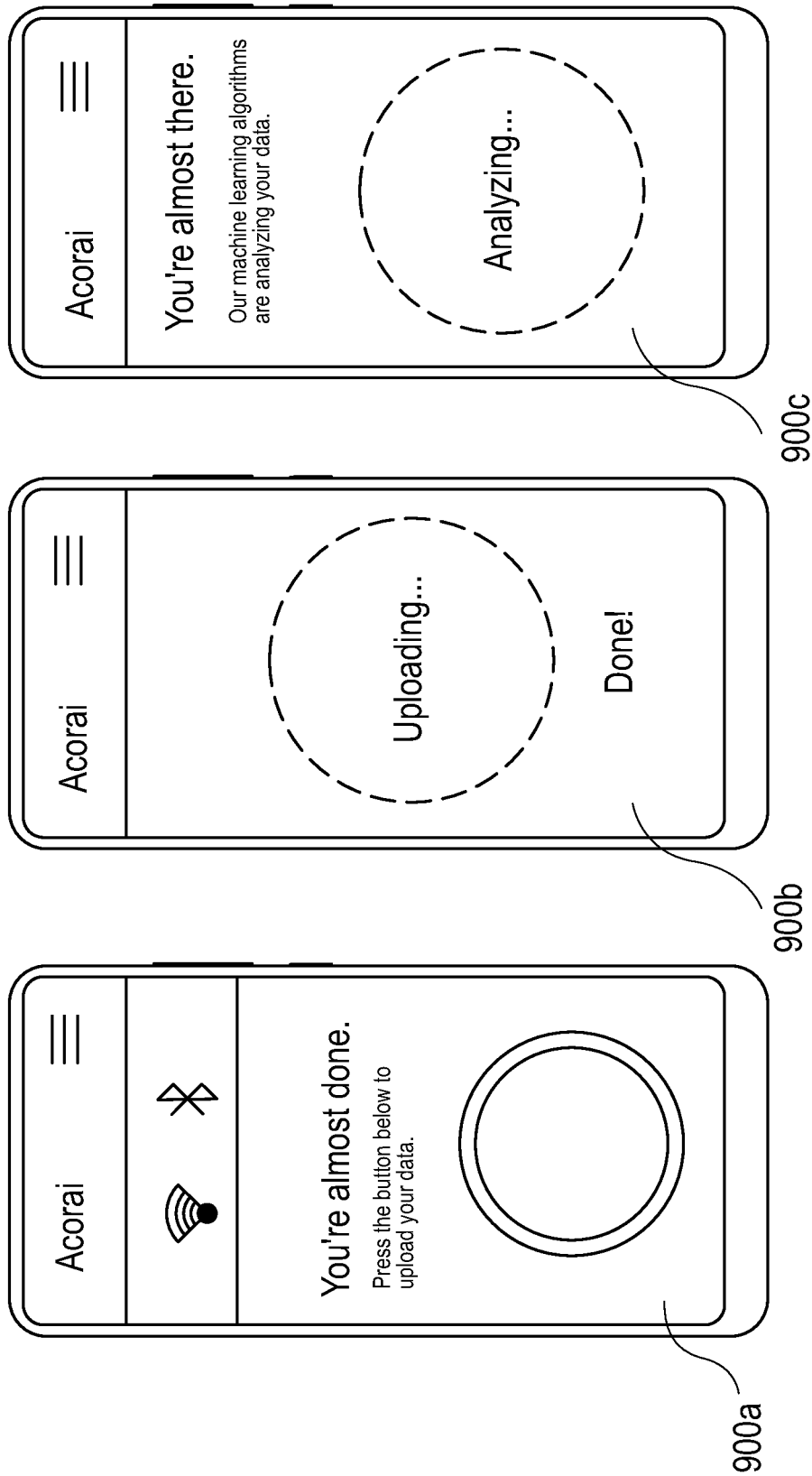

CARDIAC HEALTH ASSESSMENT SYSTEMS AND METHODS

BACKGROUND

Technical Field

The inventive subject matter presented herein is generally directed towards cardiac health assessment systems and methods for use with a handheld electronic device. More particularly, but not limited to, the subject matter relates to a cardiac health assessment system and method of analyzing heart conditions including but not limited to coronary artery disease, heart arrhythmias, pulmonary hypertension, aortic stenosis, aortic regurgitation, mitral stenosis and mitral regurgitation that is discovered using electrocardiographic, microphonic, photographic and inertial measurement unit sensors in a patient by measuring clinical indications.

Description of the Related Art

Currently, systems and methods based on Artificial Intelligence (AI) and machine learning (ML) are revolutionizing healthcare products and infrastructure. In particular, home monitoring of patients and/or early identification of health conditions, can result in markedly improved health outcomes and substantially reduce costs through preventive measures and having the ability to take earlier action to treat such conditions. Cardiac health monitoring is becoming an increasingly important part of our modern healthcare system. In the fight against increasing healthcare costs, novel patient monitoring technologies play an important part in enabling preventive healthcare to work. Cardiac disease presents one of the greatest struggles to our healthcare system.

While several invasive methods have demonstrated the efficacy in reducing heart failure re-hospitalizations based on cardiac pressure monitoring, e.g. CardioMEMS through its CHAMPION study, such devices are typically expensive costing upwards of $20,000 p.a. and require an invasive procedure. Complications related to such invasive procedures are not uncommon and may put the patient at risk. With a plethora of devices and methods being developed to perform monitoring and identify health conditions, many existing solutions are too narrow in what they are able to monitor and diagnose, thereby requiring the patient to use and keep track of a multitude of systems and devices to gain an accurate overview of their health.

Several cardiac health assessment tools in existence today are furthermore ill-suited to environments outside of a clinic. There is a need for a system and method that enable seamless patient self-use, which may be undertaken and is robust to different recording environments. Cardiac monitoring devices often contain a variety of sensors, requiring placement in certain specific ways to be accurate, something that may be difficult and time consuming for patients to apply in a self-monitoring fashion, which may discourage regular use. Sensor cables may become tangled, pulled, and damaged, causing distress to users and reducing the quality of the data collection process. Additionally, a substantial part of cardiac monitoring devices that provide continuous monitoring are limited to recording during a short period, anything from a few days up to a month. A time constraint such as this is very significant because several cardiac conditions manifest themselves and may become apparent over long periods of time, and shorter-term monitoring windows may not be able to identify such conditions. Existing traditional cardiac monitoring equipment is therefore unlikely to be satisfactory for use by patients in their homes and/or in environments outside the clinical setting.

There are more than one million hospital discharges pertaining to heart failure per annum, and, while there have been many efforts to reduce such hospitalizations, the amount has remained fairly constant over the past years. Heart failure is a condition experienced by more than 6.5 million Americans annually and causes as many as 300,000 deaths per year. Importantly, post-hospitalization, nearly one-fourth of all heart failure patients experience some form of readmission within 30 days, and at least half of these readmissions are due to heart failure. Hospitalizations such as these greatly increase mortality rates, and the risk of death increases significantly following such hospitalizations.

A large portion of commercially available solutions for cardiac monitoring is primarily focused on cardiac electrophysiology, for example electrocardiogram devices and peripheral blood volume pulse devices such as photoplethysmogram devices. While such technologies may provide estimates of heart rate, rhythm, and heart rate variability they are typically unable to provide accurate data with regard to mechanical health and vasculature of the heart. While wearable physiological technology such as impedance cardiography and finger cuff-based arterial blood pressure measurement is being explored and developed that may provide measurements of the heart's mechanical health and vasculature, the hardware needed to accurately determine factors such as cardiac output, blood pressure, cardiac contractility, and systemic vascular resistance needs a device that incorporates a wide array of sensors and is able to provide accurate health assessment of a number of cardiac conditions simultaneously.

There is a need for patient convenience to be reemphasized to create a better patient experience, and furthermore to incentivize the frequent and proper use of these technologies which is necessary when the patient themselves are in charge of said self-monitoring. Within the cardiac space there is therefore a great need for a device that can accurately measure a number of different cardiac conditions simultaneously and provide a health assessment of such conditions. There is furthermore a need to integrate such health assessment devices with consumer tech devices that are becoming omnipresent in our lives. Reducing the need to keep track of charging a health assessment device is a further added convenience that is currently lacking in existing devices. Helping patients keep track of their health assessment devices so that they do not misplace them as easily is a further need that the healthcare industry must address.

Thus, in view of the above, there is a need in the healthcare industry to address the aforementioned deficiencies and inadequacies.

SUMMARY

The inventive subject matter relates to a cardiac health assessment system and methods for use with a handheld electronic device as described in the specification and claims and as shown in and/or described in connection with at least one of the figures.

An aspect of the present disclosure relates to a cardiac health assessment system and method for use with a handheld electronic device. The cardiac health assessment system includes an electronic device case (EDC), a plurality of electrodes, and a circuit board. The electronic device case (EDC) having a shape adapted to secure the handheld electronic device with the electronic device case (EDC). The electrodes include a first ECG electrode, a second ECG electrode, and a third electrode. The first ECG electrode is placed on an outer surface of the electronic device case (EDC). The second ECG electrode and the third electrode are placed on each side of the electronic device case (EDC) to facilitate a thumb and fingers of a user to be placed on the handheld electronic device. The electrodes are configured to capture data indicative of the cardiac health of the user. The circuit board configured within the electronic device case (EDC) and electrically connected with the plurality of electrodes. The circuit board includes a microphonic sensor, a diaphragm, an Inertial Measurement Unit (IMU) sensor, and a microcontroller. The microphonic sensor captures cardiac audio signals indicative of the cardiac health of the user. The diaphragm enhances the cardiac audio signals captured by the microphonic sensor. The Inertial Measurement Unit (IMU) sensor captures seismic and auscultation signals indicative of the cardiac health of the user. The Inertial Measurement Unit (IMU) sensor comprises an IMU sensor signal enhancing material to amplify seismic and auscultation signals. The microcontroller transmits cardiac health data received from the plurality of electrodes, the microphonic sensor, and the IMU sensor to at least one of the handheld electronic device and a computing device such as a server.

In an embodiment, the handheld electronic device includes a display screen to display cardiac diagnostic information derived from the cardiac health data received from the microcontroller.

In an embodiment, the electronic device case (EDC) is positioned against the chest of the user to capture cardiac health data.

In an embodiment, the handheld electronic device comprises a processor to execute a plurality of instructions pertaining to a cardiac monitoring application. The processor is configured to display one or more commands to position the electronic device case (EDC) against the chest of the user. The processor further instructs the user (patient) to hold the electronic device case (EDC) by the user against his/her own chest using one hand.

In an embodiment, the server is configured to train a classification model to detect an abnormal heart activity arising from a plurality of parameters comprising hypertension, aortic stenosis, aortic regurgitation, mitral stenosis and/or mitral regurgitation; and train a regression model to estimate intracardiac pressure and/or left ventricular ejection fraction.

In an embodiment, the processor is configured to transmit the data indicative of cardiac function from the handheld electronic device to a server over a network; and store the data in the server for subsequent analysis by a clinician.

In an embodiment, the processor is configured to transmit the data indicative of cardiac function from the handheld electronic device to a clinician computing device via the Internet, for remote diagnostic analysis.

In an embodiment, the classification model is trained to detect abnormal heart activity arising from coronary artery disease, and heart arrhythmias.

In an embodiment, the microcontroller utilizes a de-noising algorithm, for example using a machine learning library such as TensorFlow Lite.

In an embodiment, machine learning code configured as a classification model and/or a regression model from a machine learning library, including but not limited to TensorFlow Lite, may furthermore be directly implemented within the microcontroller to assess cardiac health, thereby circumventing the need for a handheld electronic device (HED) and/or a server to be used in conjunction with the invention.

In an embodiment, the electronic device case (EDC) is adjustable to fit any handheld electronic device size.

In an embodiment, the electronic device case (EDC) is equipped with an ultrasound transducer.

In an embodiment, the electronic device case (EDC) includes a heat-sensing camera to detect variations in chest skin surface temperature resulting from variations in cardiac volume.

In an embodiment, the diaphragm includes an enhancer unit such as a bell-like object to amplify low-frequency auscultation signals pertaining to the cardiac audio signals.

In an embodiment, the electronic device case (EDC) comprises a battery configured to supply electrical power to the circuit board.

In an embodiment, the electronic device case (EDC) includes a lens configured to envelop the camera of the handheld electronic device. This allows external light to be blocked out while the electronic device shines a light into the skin of the patient and simultaneously records video and/or obtains images thereof. Based on differences in tissue color resulting from this procedure, and applying image recognition machine learning models to such pictures may provide insights into cardiac conditions.

In an embodiment, the cardiac health assessment system includes a separate handheld electronic device (HED) that includes a HED wireless transceiver, and an application. The HED wireless transceiver configured to establish a communication with a server to transmit cardiac health data therebetween. The application is programmable on the HED to transmit diagnostic information derived from cardiac health data received by the HED wireless transceiver.

An aspect of the present disclosure relates to a cardiac health assessment method for use with a handheld electronic device. The cardiac health assessment method includes a step of securing, by an electronic device case (EDC), the handheld electronic device. The cardiac health assessment method includes a step of capturing, by a plurality of electrodes, a microphonic sensor, and an Inertial Measurement Unit (IMU) sensor, cardiac health data of a user. The plurality of electrodes comprises a first ECG electrode placed on an outer surface of the electronic device case (EDC), and a second ECG electrode and a third electrode are placed on each side of the electronic device case (EDC) to facilitate a thumb and fingers of a user to be placed on the handheld electronic device. The cardiac health assessment method includes a step of transmitting, by a microcontroller, the cardiac health data received from the plurality of electrodes, the microphonic sensor, and the IMU sensor to at least one of the handheld electronic device and a computing device. The cardiac health assessment method includes a step of displaying, by a display screen, cardiac diagnostic information derived from the cardiac health data received from the microcontroller.

In an embodiment, the electronic device case (EDC) is positioned against the chest of the user to capture cardiac health data.

In an embodiment, the handheld electronic device comprises a processor to execute a plurality of instructions pertaining to a cardiac monitoring application, wherein the processor is configured to display one or more commands to position the electronic device case (EDC) against the chest of the user.

In an embodiment, the server is configured to train a classification model to detect an abnormal heart activity arising from a plurality of parameters comprising hypertension, aortic stenosis, aortic regurgitation, mitral stenosis and/or mitral regurgitation; and train a regression model to estimate intracardiac pressure and/or left ventricular ejection fraction.

In an embodiment, the classification model is trained to detect abnormal heart activity arising from coronary artery disease, and/or heart arrhythmias.

In an embodiment, the electronic device case (EDC) comprises a heat-sensing camera to detect variations in chest skin surface temperature resulting from variations in cardiac volume.

In an embodiment, the diaphragm comprises an enhancer unit to amplify low-frequency auscultation signals pertaining to the cardiac audio signals.

In an embodiment, the electronic device case (EDC) comprises a battery configured to supply electrical power to the circuit board.

In an embodiment, the electronic device case (EDC) comprises a lens configured to envelop the camera of the handheld electronic device.

In an embodiment, while recording using the electronic device case as described herein, the user is prompted by the cardiac monitoring application to make a low, continuous and/or droning sound which may advance cardiac health assessment and furthermore enable respiratory health assessment which may comprise assessing a user's lung capacity.

Accordingly, one advantage of the present invention is that it enables a non-invasive and affordable method of cardiac health assessment to identify worsening conditions of the heart and thereby substantially advance preventive home healthcare management for patients.

These features and advantages of the present disclosure may be appreciated by reviewing the following description of the present disclosure, along with the accompanying figures wherein like reference numerals refer to like parts.

BRIEF DESCRIPTION OF THE DRAWINGS

The accompanying drawings illustrate the embodiments of systems, methods, and other aspects of the disclosure. Any person with ordinary skills in the art will appreciate that the illustrated element boundaries (e.g., boxes, groups of boxes, or other shapes) in the figures represent an example of the boundaries. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope, wherein similar designations denote similar elements, and in which:

FIGS. 8a-8c illustrate a plurality of user interfaces to depict a plurality of directions pertaining to the usage of the electronic device case (EDC), in accordance with at least one embodiment.

FIGS. 9a-9c illustrate a plurality of user interfaces to depict a plurality of operations performed by the mobile application, in accordance with at least one embodiment.

DETAILED DESCRIPTION

The present description is best understood with reference to the detailed figures and description set forth herein. Various embodiments of the present system and method have been discussed with reference to the figures. However, those skilled in the art will readily appreciate that the detailed description provided herein with respect to the figures are merely for explanatory purposes, as the present system and method may extend beyond the described embodiments. For instance, the teachings presented and the needs of a particular application may yield multiple alternative and suitable approaches to implement the functionality of any detail of the present systems and methods described herein. Therefore, any approach to implement the present system and method may extend beyond certain implementation choices in the following embodiments.

According to an embodiment herein, the methods of the present claimed subject matter may be implemented by performing or completing manually, automatically, and/or a combination of thereof. The term "method" refers to manners, means, techniques and procedures for accomplishing any task including, but not limited to, those manners, means, techniques, and procedures either known to the person skilled in the art or readily developed from existing manners, means, techniques and procedures by practitioners of the art to which the present invention belongs. The persons skilled in the art will envision many other possible variations within the scope of the present system and method described herein.

Figure 1:
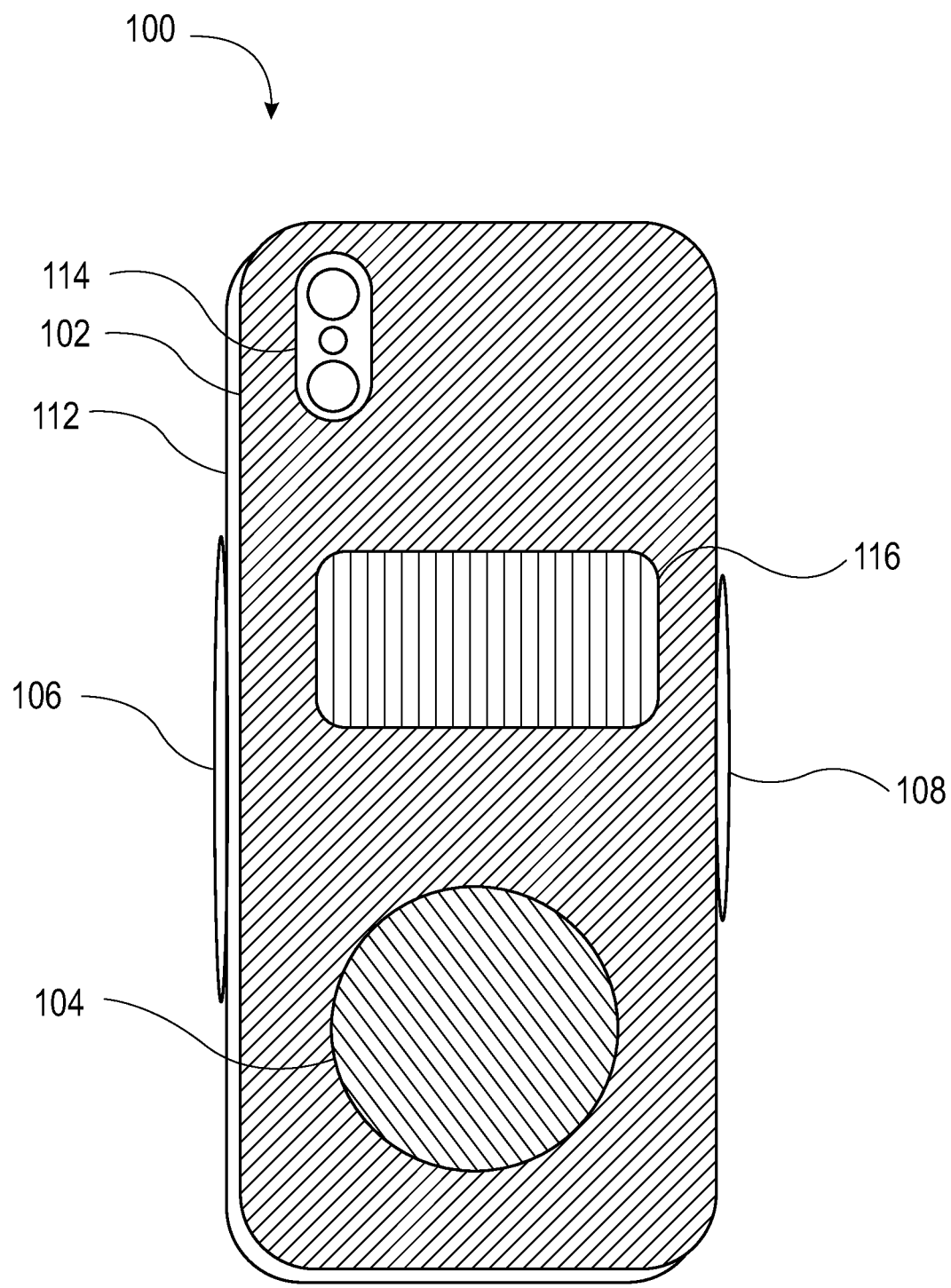
FIG. 1 illustrates a perspective view of the various components of the present cardiac health assessment system for use with a handheld electronic device, in accordance with at least one embodiment.

FIG. 1 illustrates a perspective view 100 of the various components of the present cardiac health assessment system for use with a handheld electronic device, in accordance with at least one embodiment. The cardiac health assessment system includes an electronic device case (EDC) 102, a plurality of electrodes 104, 106, and 108, and a circuit board 110 (shown in FIG. 2). The electronic device case (EDC) 102 having a shape adapted to secure the handheld electronic device 112 with the electronic device case (EDC) 102. The shape of the electronic device case (EDC) 102 can be adapted for the handheld electronic device 112 such as a mobile phone or smartphone so that the handheld electronic device can fit and be secured into the electronic device case (EDC) 102. The electrodes include a first ECG electrode 104, a second ECG electrode 106, and a third electrode 108. The first ECG electrode 104 is placed on an outer surface of the electronic device case (EDC) 102. The second ECG electrode 106 and the third electrode 106 are placed on each side of the electronic device case (EDC) 102 to facilitate a thumb and fingers of a user to be placed on the handheld electronic device 112. The electrodes 104, 106, and 108 are configured to capture data indicative of the cardiac health of the user.

Figure 2:
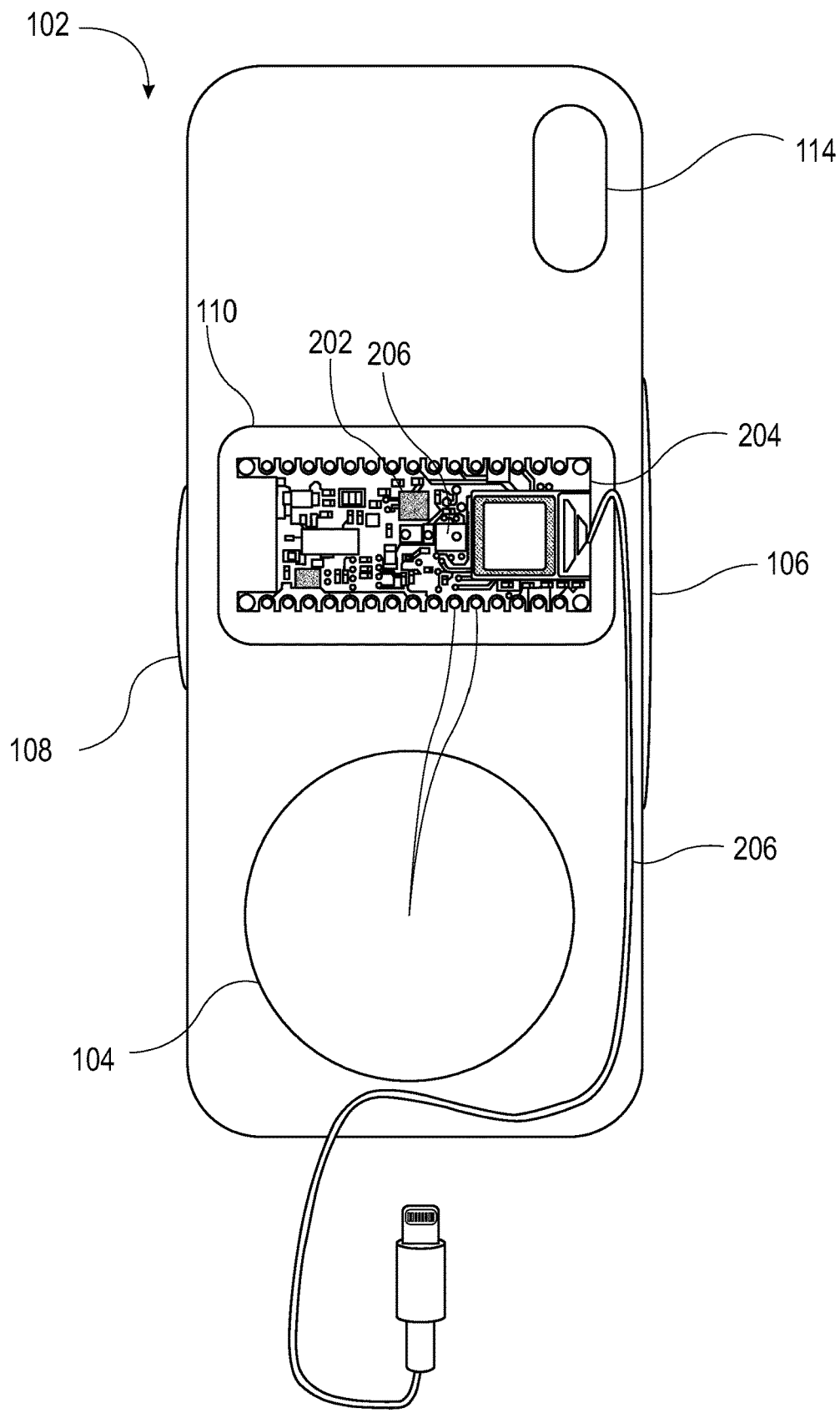
FIG. 2 illustrates an exploded view of the various components of the electronic device case (EDC), in accordance with at least one embodiment.

FIG. 2 illustrates an exploded view of the various components of the electronic device case (EDC) 102, in accordance with at least one embodiment. FIG. 2 is explained in conjunction with FIG. 1. The circuit board 110 is configured within the electronic device case (EDC) 102 and electrically connected with the plurality of electrodes 104, 106, and 108. The circuit board 110 includes a microphonic sensor 202, a diaphragm 204, an Inertial Measurement Unit (IMU) sensor 206, and a microcontroller. In an embodiment, the electronic device case (EDC) is adjustable to fit any handheld electronic device size. In an embodiment, the electronic device case (EDC) is equipped with an ultrasound transducer. In an embodiment, the electronic device case (EDC) includes a heat-sensing camera to detect variations in chest skin surface temperature resulting from variations in cardiac volume. The microphonic sensor 202 captures cardiac audio signals indicative of the cardiac health of the user. The diaphragm 204 enhances the cardiac audio signals captured by the microphonic sensor 202. In an embodiment, the diaphragm 204 includes an enhancer unit such as a bell-like object to amplify low-frequency auscultation signals pertaining to the cardiac audio signals. In an embodiment, the diaphragm 204 may be configured as a tube structure to enhance low-frequency sounds. The tube structure may look like the bell used in a regular stethoscope (instead of a diaphragm). The Inertial Measurement Unit (IMU) sensor 206 captures seismic and auscultation signals indicative of the cardiac health of the user. The Inertial Measurement Unit (IMU) sensor 206 comprises an IMU sensor signal enhancing material 116 to amplify seismic and auscultation signals. Examples of the IMU sensor signal enhancing material may include but is not limited to sound absorbers made from porous materials, micro-perforated plates and/or micro-perforated panel absorbers backed with mechanical impedance plates where the backed cavity is limited.

Figure 3:
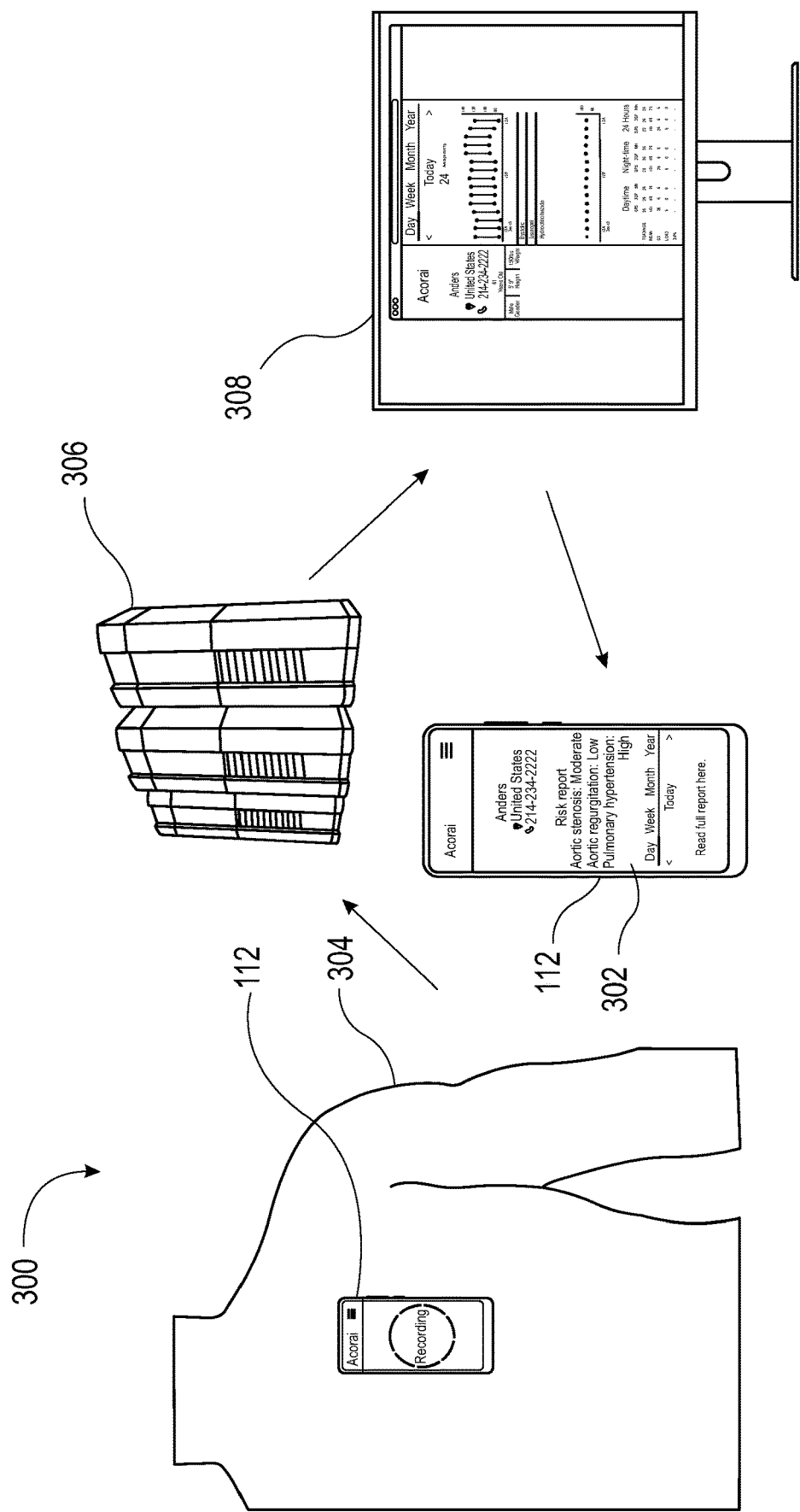
FIG. 3 illustrates a network implementation of the present cardiac health assessment system, in accordance with at least one embodiment.

The microcontroller transmits cardiac health data received from the plurality of electrodes 104, 106, and 108, the microphonic sensor 202, and the IMU sensor 206 to at least one of the handheld electronic device 112 and a computing device such as a server 306 (shown in FIG. 3). In an embodiment, the electronic device case (EDC) 102 includes a lens 114 configured to envelop the camera of the handheld electronic device 112. This allows external light to be blocked out while the handheld electronic device 112 shines a light into the skin of the patient and simultaneously records video and/or obtains images thereof. Based on differences in tissue color resulting from this procedure, and applying image recognition machine learning models to such pictures may provide insights into cardiac conditions. Increased left atrial pressure is for example known to be correlated with left atrial volume, and may, therefore, cause differences in tissue color resulting from excess blood pressure present in different parts of the cardiac system. Such videos and/or images may furthermore uncover micro perturbations in the flow of blood that may be indicative of certain cardiac conditions such as elevated cardiac pressure. In an embodiment, the electronic device case (EDC) 102 comprises a battery configured to supply electrical power to the circuit board, wherein the battery may receive power supply from an external source. The electronic device case (EDC) 102 may connect with the handheld electronic device 112 through a power cable 206.

FIG. 3 illustrates a network implementation of the present cardiac health assessment system 300, in accordance with at least one embodiment. In an embodiment, the handheld electronic device 112 includes a display screen 302 to display cardiac diagnostic information derived from the cardiac health data received from the microcontroller. In an embodiment, the electronic device case (EDC) configured with the handheld electronic device 112 is positioned against the chest of the user 304 to capture cardiac health data. In an embodiment, the handheld electronic device 112 comprises a processor to execute a plurality of instructions pertaining to a cardiac monitoring application. The processor is configured to display one or more commands to position the electronic device case (EDC) against the chest of the user. The processor further instructs the user (patient) to hold the electronic device case (EDC) by the user against his/her own chest using one hand.

In an embodiment, the server 306 trains a classification model to detect an abnormal heart activity arising from a plurality of parameters comprising hypertension, aortic stenosis, aortic regurgitation, mitral stenosis, and/or mitral regurgitation. The server 306 may further train a regression model to estimate intracardiac pressure and/or left ventricular ejection fraction. According to an embodiment herein, the server 306 is configured to train the classifier model and/or the regression model based on the identified data relationships in a secure database; receive a representation of the inertial measurement unit (IMU) sensor, and/or electrode and/or microphonic sensor signal recorded by the electronic device case (EDC) during temporal windows; detect the features of said sensors in at least some of the portions of the representation falling within each of the temporal windows; use the trained classifier model and/or regression model to identify patterns of said sensor features within the portions of said sensor signals; for each of the portions, calculate a probability of whether the portion of the representation within said sensor signals is associated with a patient experiencing cardiac health problems and/or estimating cardiac measurement values; and take an action based on the score.

In an embodiment, the processor is configured to transmit the data indicative of cardiac function from the handheld electronic device 112 to a server 306 over a network; and store the data in the server 306 for subsequent analysis by a clinician. Examples of the network could be a combination of a local area network and a wide area network, such as the Internet, through a physical or a wireless connection, for example, Bluetooth. In an embodiment, the processor is configured to transmit the data indicative of cardiac function from the handheld electronic device 112 to a clinician computing device 308 via the Internet, for remote diagnostic analysis using ML. In an embodiment, the clinician computing device 308 performs risk analysis and present in the mobile application of the handheld electronic device 112 in a suitable/presentable format. In an embodiment, the classification model is trained to detect abnormal heart activity arising from one or more cardiac health conditions comprising coronary artery disease and heart arrhythmias. In an embodiment, the microcontroller utilizes a pre-trained de-noising algorithm, for example using a machine learning library such as TensorFlow Lite.

Figure 4:
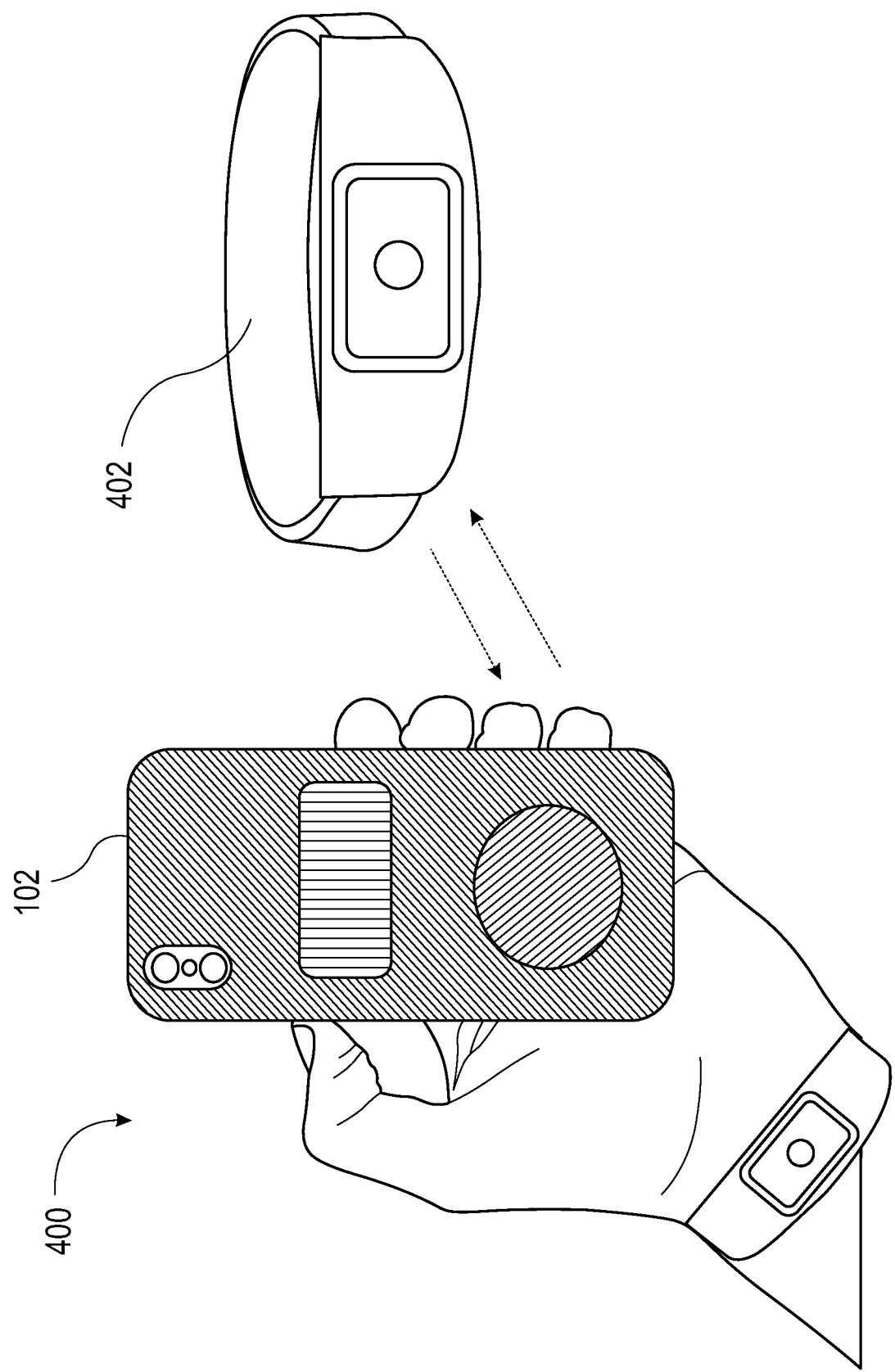
FIG. 4 illustrates a perspective view of communication between the electronic device case (EDC) and a separate handheld electronic device (HED), in accordance with at least one embodiment.
Figure 5:
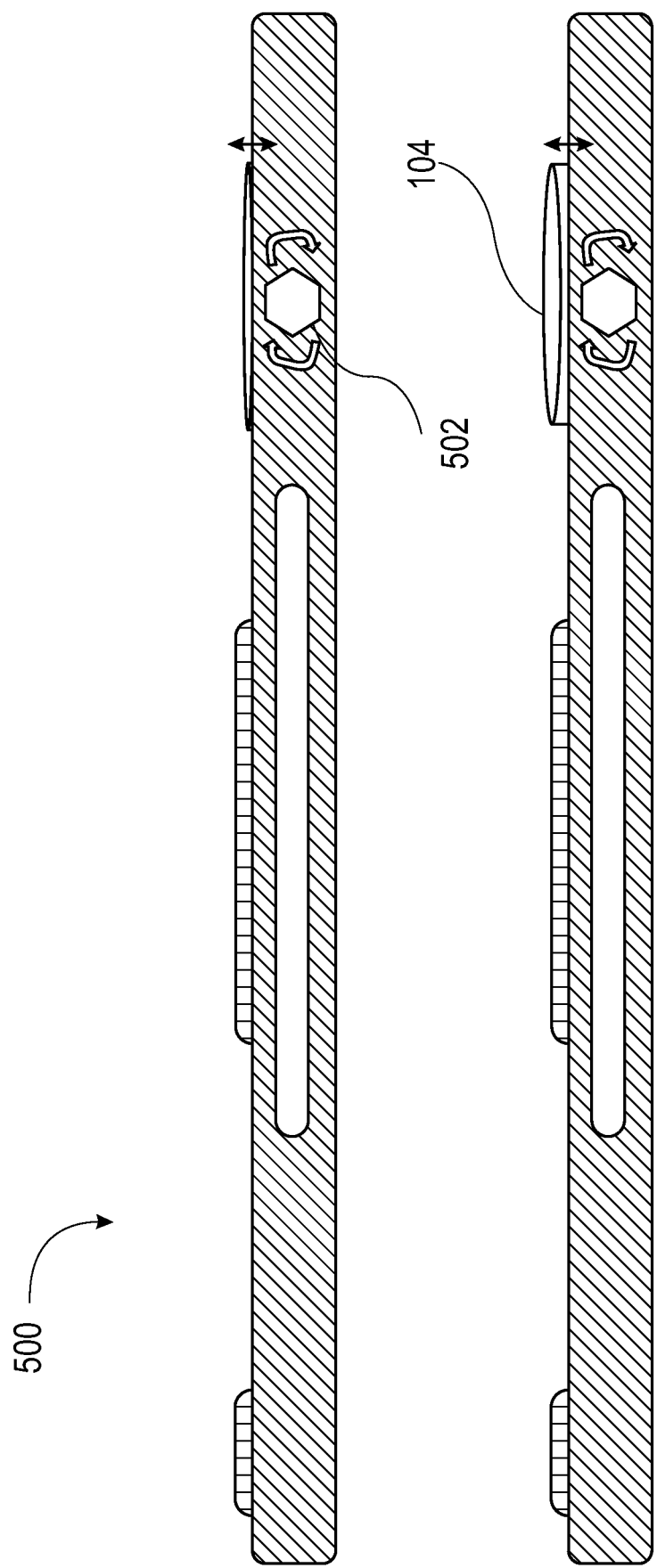
FIG. 5 illustrates a side view of the electronic device case (EDC), in accordance with at least one embodiment.

FIG. 4 illustrates a perspective view 400 of communication between the electronic device case (EDC) 102 and a separate handheld electronic device (HED) 402, in accordance with at least one embodiment. In an embodiment, the cardiac health assessment system includes a separate handheld electronic device (HED) 402 that includes a HED wireless transceiver, and an application. The HED wireless transceiver receives cardiac health data from the electronic device case (EDC) 102 and establishes a communication with a server to transmit the cardiac health data therebetween. The application is programmable on the HED to transmit diagnostic information derived from cardiac health data received by the HED wireless transceiver. In an embodiment, the separate handheld electronic device (HED) 402 is a wearable device which can connect wirelessly with the handheld electronic device 112, such as "smartphones", "smartwatches," PCs, tablets, or handheld computers to simultaneously download and examine data in real-time and/or in a different temporal segment. FIG. 5 illustrates a side view 500 of the electronic device case (EDC), in accordance with at least one embodiment. According to an embodiment herein, the electronic device case (EDC) includes a button 502 such as a toggle like a button to initiate the operation (in/out) of the first ECG electrode 104.

Figure 6:
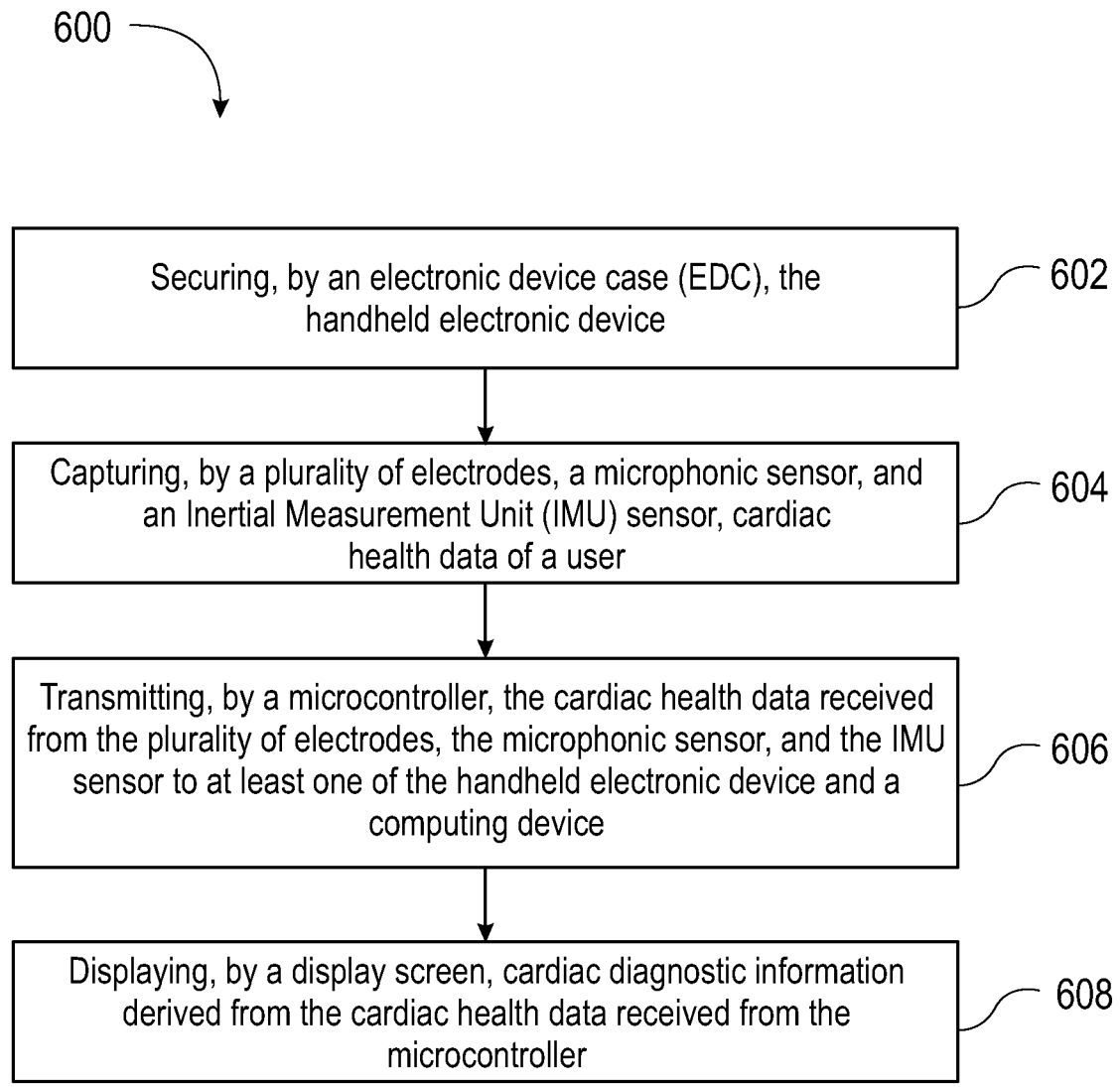
FIG. 6 illustrates a flowchart of the present cardiac health assessment method for use with a handheld electronic device, in accordance with at least one embodiment.

FIG. 6 illustrates a flowchart of the present cardiac health assessment method for use with a handheld electronic device, in accordance with at least one embodiment. The cardiac health assessment method includes a step 602 of securing, by an electronic device case (EDC), the handheld electronic device. The cardiac health assessment method includes a step 604 of capturing, by a plurality of electrodes, a microphonic sensor, and an Inertial Measurement Unit (IMU) sensor, cardiac health data of a user. The plurality of electrodes comprises a first ECG electrode placed on an outer surface of the electronic device case (EDC), and a second ECG electrode and a third electrode are placed on each side of the electronic device case (EDC) to facilitate a thumb and fingers of a user to be placed on the handheld electronic device. The cardiac health assessment method includes a step 606 of transmitting, by a microcontroller, the cardiac health data received from the plurality of electrodes, the microphonic sensor, and the IMU sensor to at least one of the handheld electronic device and a computing device. The cardiac health assessment method includes a step 608 of displaying, by a display screen, cardiac diagnostic information derived from the cardiac health data received from the microcontroller. In an embodiment, the electronic device case (EDC) is positioned against the chest of the user to capture cardiac health data. In an embodiment, the electronic device case (EDC) comprises a heat-sensing camera to detect variations in chest skin surface temperature resulting from variations in cardiac volume. In an embodiment, the diaphragm comprises an enhancer unit to amplify low-frequency auscultation signals pertaining to the cardiac audio signals. In an embodiment, the electronic device case (EDC) comprises a lens configured to envelop the camera of the handheld electronic device.

In an embodiment, the handheld electronic device comprises a processor to execute a plurality of instructions pertaining to a cardiac monitoring application, wherein the processor is configured to display one or more commands to position the electronic device case (EDC) against the chest of the user. In an embodiment, the server is configured to train a classification model to detect an abnormal heart activity arising from a plurality of parameters comprising hypertension, aortic stenosis, aortic regurgitation, mitral stenosis and/or mitral regurgitation; and train a regression model to estimate intracardiac pressure and/or left ventricular ejection fraction. In an embodiment, the classification model is trained to detect abnormal heart activity arising from coronary artery disease and/or heart arrhythmias.

The present cardiac health assessment system and method may include more than three different types of sensors employing different technologies as presented herein, which furthermore allows for robustness across different recording environments and patient cohorts. In one example of this, in a noisy environment, one might rely more heavily on visual or seismic sensors, whereas in a patient with darker skin where light is less able to penetrate adequately, one might rely more heavily on sensors pertaining to audio or electrophysiological sensors.

According to an embodiment herein, the present cardiac health assessment system and method provide an ability to operate the electronic device case (EDC) without a battery and through direct power from an electronic device improves on existing products of cardiac health assessment in several ways. Such a configuration allows for more space, and therefore larger and more powerful sensors may be used in the invention, further enhancing data collection quality and accuracy. The absence of a battery may furthermore reduce the amount of electrical interference inherent to the EDC's sensors. This allows for a more powerful device, removing the necessity of having multiple devices in order to be able to identify different cardiac conditions. Through having one device that is able to accurately analyze a number of the cardiac conditions instead of just a few, the patient experience is substantially improved, potentially increasing the patient's ease and willingness of carrying out monitoring on a regular basis.

The utilization of a handheld electronic device (HED) to use the EDC furthermore improves the accuracy of the EDC in one or more ways. Using the HED's internal accelerometer and microphone sensors, external data noise pertaining to both movement and sound can be measured. Such measurement can be of aid in the process of removing noise from the data so that the analysis can be made on data that is most relevant to conditions pertaining to cardiac health.

With increased electronic device usage globally, particularly with regard to smartphones, an EDC as presented herein is likely to substantially simplify the self-monitoring process for the patient. The present cardiac health assessment system and method are designed to always be carried with the patient, for example in the form as a protective case for a smartphone. Having one device instead of multiple for the purpose of cardiac self-monitoring likely reduces the propensity to misplace said device and having the ability to rely on the battery power of the electronic device further increases the likelihood of the device being charged at the right times. It further simplifies the ability to record at standardized time intervals. For example, a patient may use a handheld electronic device's internal alarm clock which might simultaneously remind and prompt the patient to do their cardiac health assessment recording using the EDC. Having the recording carried out at approximately the same time each day may further simplify the data analysis by being able to compare more similar recording environments. This may standardize the data collection process and consequently help reduce data noise.

Figure 7:
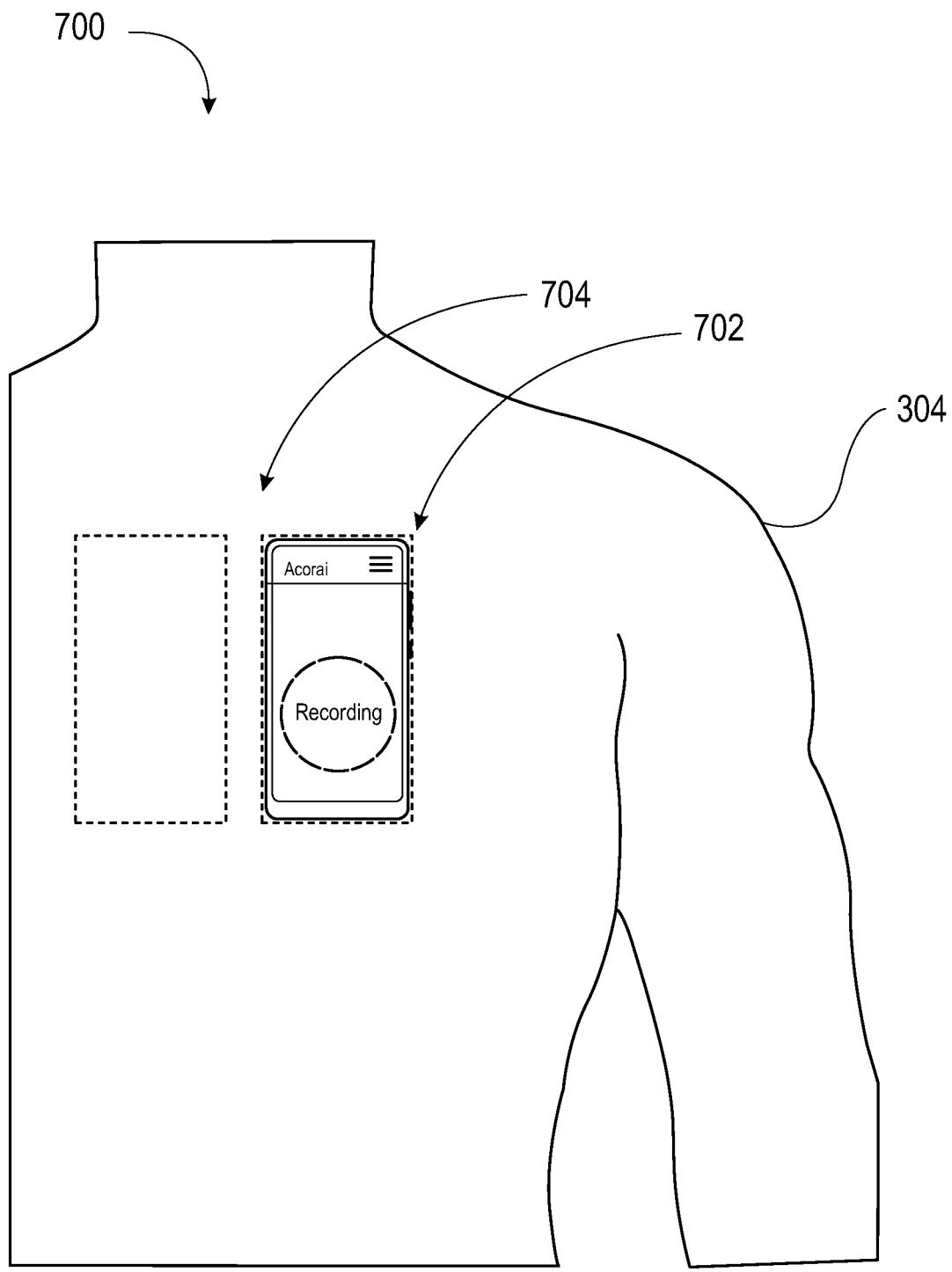
FIG. 7 illustrates a perspective view of the placement of the electronic device case (EDC) on the patient's chest, in accordance with at least one embodiment.

FIG. 7 illustrates a perspective view of the placement of the electronic device case (EDC) 102 on the patient's chest, in accordance with at least one embodiment. The EDC is placed centrally on the patient's chest. In some embodiments of the present invention, the software application executed on the mobile phone may be used to direct the user of the electronic device case to correct placement upon their chest. Directions originating from the application may comprise a first step 702 to place the electronic device case (EDC) a finger below the patient's left collarbone, alongside the sternum and then in second step 704, placing the EDC one finger below the patient's right collarbone alongside the sternum. FIGS. 8a-8c illustrate a plurality of user interfaces 800a, 800b, and 800c to depict a plurality of directions pertaining to the usage of the electronic device case (EDC), in accordance with at least one embodiment. The user interface 800a depicts the first step to the user to place the handheld electronic device a finger below the patient's left collarbone and press the 'Step 1' button below to start recording, shown in user interface 800b. The user has to keep recording until the software application notifies/announces the user to stop. After recording, the user interface 800c depicts "Step 1 complete!" and instructs the user to place the smartphone firmly on his/her right chest, just below the collarbone, and press the 'Step 2' button below to start recording. Again, the user has to keep recording until the software application notifies/announces the user to stop.

FIGS. 9a-9c illustrate a plurality of user interfaces 900a, 900b, and 900c to depict a plurality of operations performed by the mobile application, in accordance with at least one embodiment. The user interface 900a depicts that the mobile application facilitates the user to upload the cardiac health data received from the plurality of electrodes, the microphonic sensor, and the IMU sensor. The user interface 900b depicts the uploading process of cardiac health data. The user interface 900c depicts the mobile application analyzes the cardiac health data to figure out where it is most ideal to place the electronic device case (EDC) can furthermore help standardize data collection quality across different patient cohorts. The mobile application remembers certain features associated with the patient's cardiac signup and a certain position and indicates when the patient might have placed the EDC in the wrong location and furthermore prompt the patient to reposition the EDC.

In some embodiments of the invention, the data collected through the EDC may be combined with data from a wearable electronic device. By combining data from other sources, such as a wearable sensor on the wrist of a patient, one may further enhance accuracy, for example by having the ability to calculate pulse transit time, and compare data between different parts of the body at the same time. Such combinations may further diversify the type of data and add robustness to the data collection process by combining a broader variety of sensor technologies such as but not limited to photoplethysmography. In some embodiments of the invention, the EDC may be equipped with a wireless charging station to allow for wireless charging of other devices/wearables. A battery-less wearable may be connected to the EDC and used to simultaneously record data, drawing power from the EDC.

Upon completing the data recording from the patient, the data may be analyzed in the connected electronic device or uploaded to a server for further analysis there. Said data analysis includes but is not limited to machine learning-based methods to classify whether or not certain cardiac conditions such as but not limited to, hypertension, reduced left ventricular ejection fraction, heart arrhythmias, aortic stenosis, aortic regurgitation, mitral stenosis, mitral regurgitation and/or coronary artery disease was present. The data analysis portion may furthermore be comprised of estimating cardiac pressure and the heart's left ventricular ejection fraction. The machine learning methods may include but are not limited to decision tree-based machine learning methods, artificial neural networks, convolutional neural networks, logistic regression, naive Bayes, nearest neighbor, support vector machines, and boosted tree learning methods.

Figure 10:
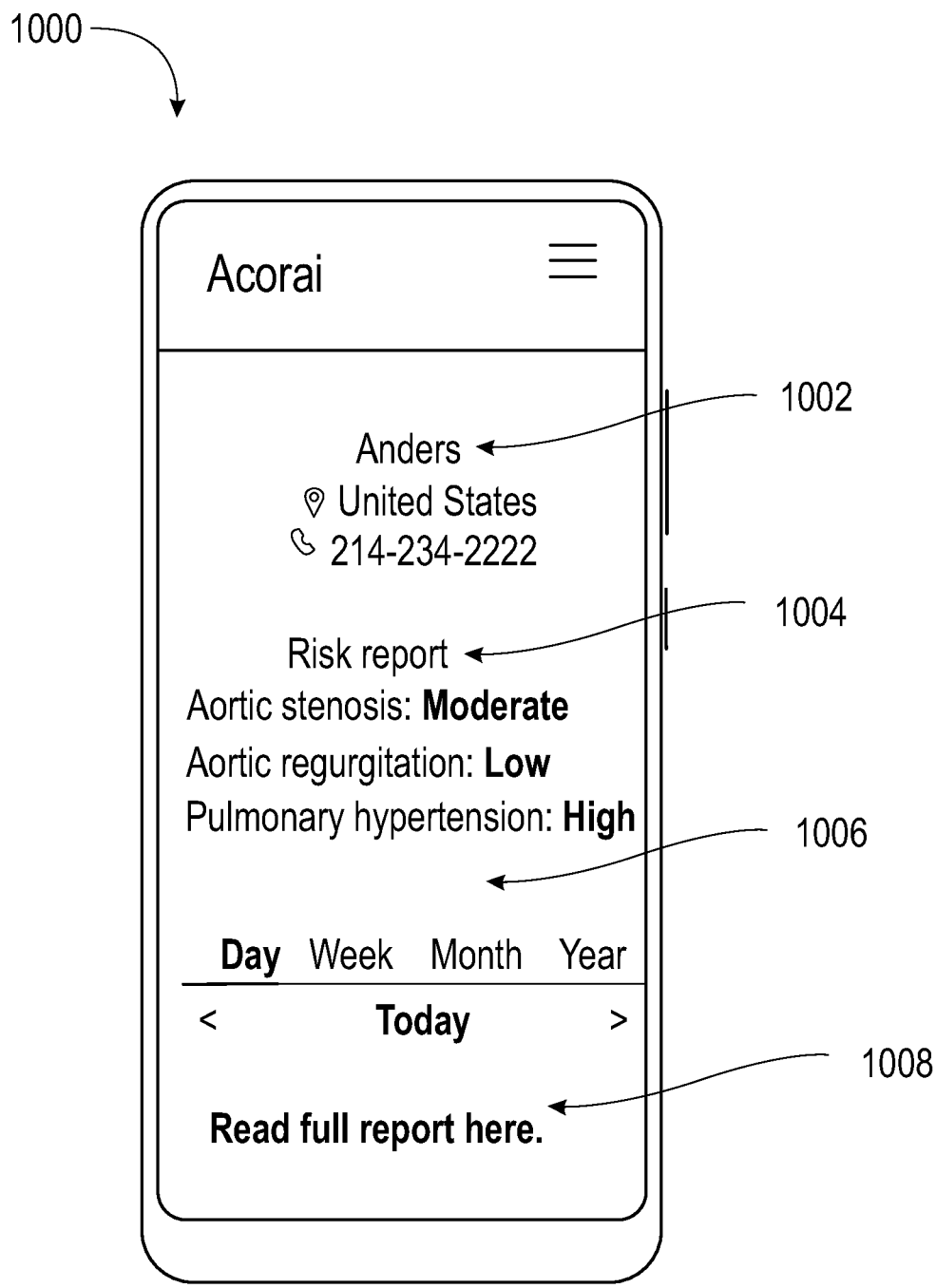
FIG. 10 illustrates a user interface to depict personal information and cardiac diagnostic information pertaining to the user, in accordance with at least one embodiment.

FIG. 10 illustrates a user interface 1000 to depict personal information and cardiac diagnostic information pertaining to the user, in accordance with at least one embodiment. The results of the data analysis are presented through the mobile application to the patient and/or in any other way to a person of the patient's choice. For example, an email might be sent to the patient's clinician with a report of the recording. At block 1002, the user interface 1000 depicts patient name and contact information. At block 1004, the user interface 1000 depicts the results from the analysis of the cardiac health data. At block 1006, the user interface 1000 depicts that the user can view and compare past recordings. At block 1008, the user interface 1000 depicts that the physician can manually see and listen to each recording.

Figure 11:
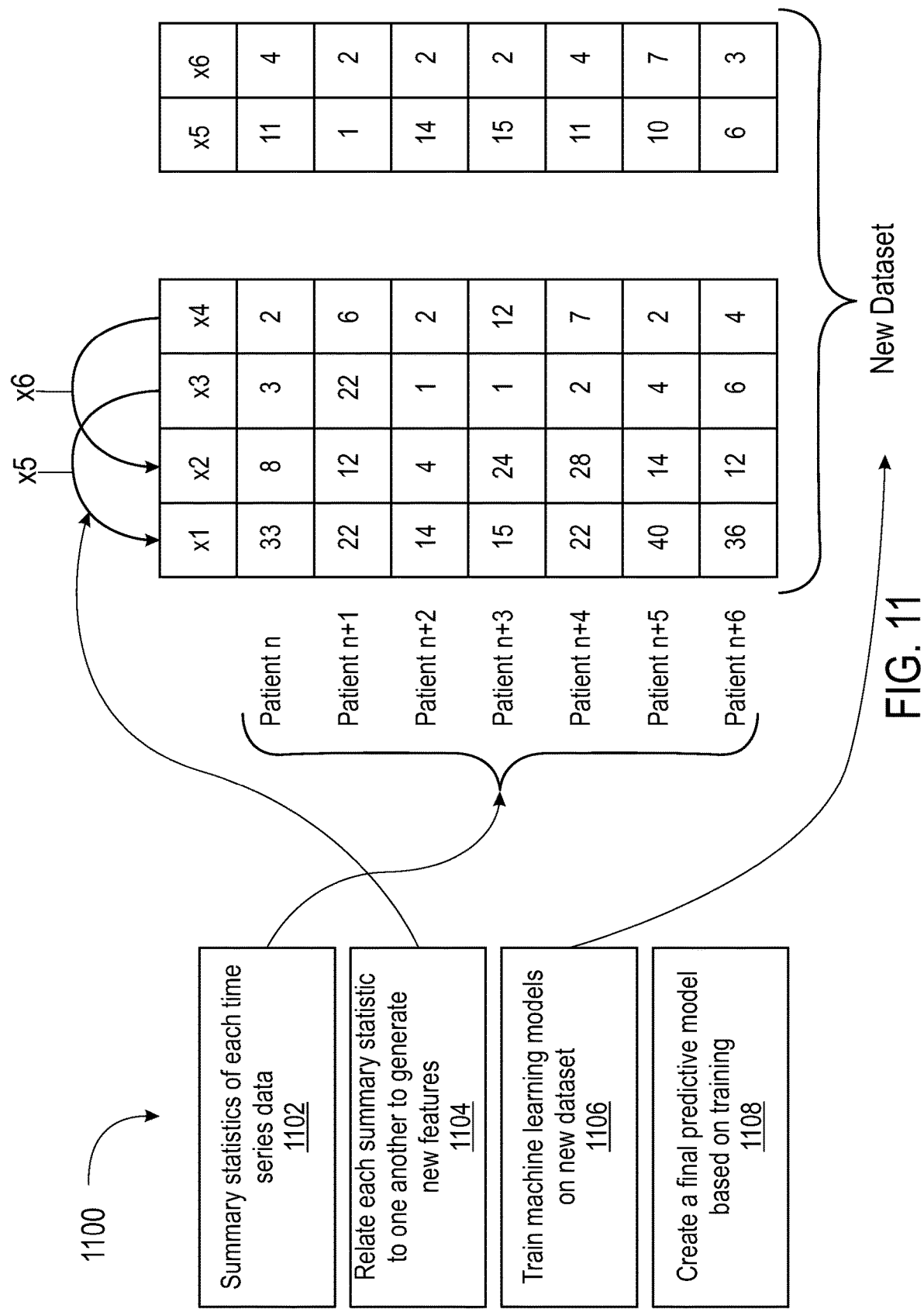
FIG. 11 illustrates a flow diagram of feature generation through a division of columns by one another, in accordance with at least one embodiment.

FIG. 11 illustrates a flow diagram 1100 of feature generation through a division of columns by one another, in accordance with at least one embodiment. At step 1102, the summary statistics of each time series data pertaining to a plurality of the patients have been fed. At step 1104, the flow diagram relates each summary statistic to one another to generate new features. At step 1106, machine learning models are trained on a new dataset. At step 1108, a final predictive model is created based on the training of the machine learning models.

Unless otherwise defined, all terms (including technical and scientific terms) used in this disclosure have the same meaning as commonly understood by one of ordinary skill in the art to which this disclosure belongs. It is to be understood that the phrases or terms employed of the present invention is for the purpose of description and not of limitation. As will be appreciated by one of skill in the art, the present disclosure may be embodied as a device, system, and method or computer program product. Further, the present invention may take the form of a computer program product on a computer-readable storage medium having computer-usable program code embodied in the medium. The present systems and methods have been described above with reference to specific examples. However, other embodiments and examples than the above description are equally possible within the scope of the present invention. The scope of the disclosure may only be limited by the appended patent claims. Even though modifications and changes may be suggested by the persons skilled in the art, it is the intention of the inventors and applicants to embody within the patent warranted heron all the changes and modifications as reasonably and properly come within the scope of the contribution the inventors and applicants to the art. The scope of the embodiments of the present invention is ascertained with the claims to be submitted at the time of filing the complete specification.

What is claimed is:

1. A cardiac health assessment system for use with a handheld electronic device, the cardiac health assessment system comprising:
   a handheld electronic device having a processor configured to transmit data indicative of cardiac function from the handheld electronic device to one or more computing devices over a network for remote diagnostic analysis using machine learning;
   an electronic device case (EDC) having a shape adapted to position the handheld electronic device within the EDC;

a plurality of electrodes comprising:
- a first ECG electrode placed on an outer surface of the EDC; and
- a second ECG electrode and a third electrode placed on the sides of the EDC to facilitate a thumb and fingers of a user to be placed on the EDC having the shape that is adapted to secure the handheld electronic device, wherein the plurality of electrodes are configured to capture data indicative of the cardiac health of a user; and a circuit board configured within the EDC and electrically connected with the plurality of electrodes, wherein the circuit board comprises:
- a microphonic sensor to capture cardiac audio signals indicative of the cardiac health of the user;
- a diaphragm to enhance the cardiac audio signals captured by the microphonic sensor,
- an Inertial Measurement Unit (IMU) sensor to capture seismic and auscultation signals indicative of the cardiac health of the user, wherein the IMU sensor includes an IMU sensor signal-enhancing material to amplify seismic and auscultation signals; and
- a microcontroller to transmit cardiac health data received from the plurality of electrodes, the microphonic sensor, and the IMU sensor to at least one of the handheld electronic device and a computing device, wherein the computing device is configured to:
  - receive, in one or more temporal windows, a representation of one or more of the IMU sensor, the plurality of electrodes, and the microphonic sensor signal recorded by the EDC;
  - detect features of the IMU sensor, the plurality of electrodes and the microphonic sensor from at least one or more portions of the received representations falling within each of the one or more temporal windows;
  - identify patterns of the features of respective sensors and electrodes from within the one or more portions based on at least a trained classification model or a regression model;
  - calculate, based on the identified patterns, a probability of whether the one or more portions correspond to a problem with the cardiac health of the user; and
  - estimate, based on the identified patterns, one or more of the following: an intracardiac pressure of the user and left ventricular ejection fraction of the user.

2. The cardiac health assessment system according to claim 1, wherein the handheld electronic device includes a display screen for displaying cardiac diagnostic information derived from the cardiac health data received from the microcontroller.

3. The cardiac health assessment system according to claim 1, wherein the EDC is configured to capture cardiac health data of the user when positioned against the chest of the user.

4. The cardiac health assessment system according to claim 1, wherein the processor executes a plurality of instructions pertaining to a cardiac monitoring application, and wherein the processor is configured to show on the display one or more commands allowing the user to position the EDC against the chest of the user.

5. The cardiac health assessment system according to claim 1, wherein the trained classification model is trained using the cardiac health data received from the plurality of electrodes, the microphonic sensor, and the IMU sensor for aiding in the detection of abnormal heart activity arising from cardiac health conditions comprising coronary artery disease and heart arrhythmias.

6. The cardiac health assessment system according to claim 1, wherein the EDC further comprises a heat-sensing camera to detect variations in chest skin surface temperature resulting from variations in cardiac volume.

7. The cardiac health assessment system according to claim 1, wherein the diaphragm further comprises an enhancer unit to amplify low-frequency auscultation signals pertaining to the cardiac audio signals.

8. The cardiac health assessment system according to claim 1, wherein the EDC further comprises a battery configured to supply electrical power to the circuit board.

9. The cardiac health assessment system according to claim 1, wherein the EDC further comprises a camera and a lens configured to envelop at least a portion of the camera.

10. The cardiac health assessment system according to claim 1 further comprising a second computing device wirelessly connected to the handheld electronic device and having a wireless transceiver configured to establish communication with the handheld electronic device for communicating cardiac health data there-between, wherein the second computing device is configured to:
- detect using a classification model an abnormal heart activity arising from a plurality of parameters comprising one or more of: hypertension, aortic stenosis, aortic regurgitation, mitral stenosis, and mitral regurgitation; and
- estimate using a regression model one or more of: an intracardiac pressure and a left ventricular ejection fraction.

11. The cardiac health assessment system according to claim 9, wherein the lens is configured to block external environmental light when the handheld electronic device shines a light on the skin of the user, wherein the lens is used to record one or more images of the user's skin, and wherein the one or more images of the user's skin are analyzed with machine learning to provide insights into the cardiac health of the user.

* * * * *